(12) United States Patent
Andreacchi

(10) Patent No.: US 6,679,980 B1
(45) Date of Patent: Jan. 20, 2004

(54) APPARATUS FOR ELECTROPOLISHING A STENT

(75) Inventor: Anthony Andreacchi, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 110 days.

(21) Appl. No.: 09/881,166

(22) Filed: Jun. 13, 2001

(51) Int. Cl.[7] .................................................. C25F 7/00
(52) U.S. Cl. ...................................... 204/272; 204/242
(58) Field of Search ................................ 204/194, 242, 204/272, 280

(56) References Cited

U.S. PATENT DOCUMENTS

| | | | |
|---|---|---|---|
| 3,556,883 A | | 1/1971 | Naito et al. |
| 3,645,857 A | * | 2/1972 | Fisher et al. ................. 205/138 |
| 3,986,970 A | | 10/1976 | Shiga |
| 4,048,048 A | * | 9/1977 | Bennett et al. .............. 204/279 |
| 4,290,867 A | * | 9/1981 | Jumer ......................... 205/686 |
| 4,367,127 A | * | 1/1983 | Messing et al. ............. 205/566 |
| 5,158,548 A | | 10/1992 | Lau et al. |
| 5,217,586 A | * | 6/1993 | Datta et al. .................. 205/666 |
| 5,344,425 A | | 9/1994 | Sawyer |
| 5,421,955 A | | 6/1995 | Lau et al. |
| 5,514,154 A | | 5/1996 | Lau et al. |
| 5,605,611 A | * | 2/1997 | Ozawa et al. ................ 204/242 |
| 5,750,434 A | | 5/1998 | Urushidani et al. |
| 5,972,180 A | * | 10/1999 | Chujo .................... 204/224 M |
| 5,997,703 A | * | 12/1999 | Richter ..................... 204/297.1 |
| 6,019,784 A | | 2/2000 | Hines |
| 6,131,266 A | | 10/2000 | Saunders |
| 6,375,826 B1 | * | 4/2002 | Wang et al. ................. 205/684 |
| 2002/0023843 A1 | * | 2/2002 | Cherkes ........................ 205/75 |

OTHER PUBLICATIONS

*Standard Guide for Electrolytic Polishing of Metallographic Specimens*, American Society and Materials (Designation: E 1558–93), pp. 1–12, 1993.
*Standard Practice for Microetching Metal and Alloys*, American Society and Materials (Designation: E 407–93), pp. 1–18, 1993.
*Standard Test Method for Macroetching Metals and Alloys*, American Society and Materials (Designation: E 340–93), pp. 1–10, 1993.
Surman, Harmut et al., *Automatic Electropolishing of Cobalt Chromium Dental Cast Alloys With a Fuzzy Logic Controller*, Computers Chemical Engineering, vol. 22, No. 7–8, pp. 1099–1111, 1998.

* cited by examiner

*Primary Examiner*—Nam Nguyen
*Assistant Examiner*—Brian L Mutschler
(74) *Attorney, Agent, or Firm*—Fulwider Patton Lee & Utecht, LLP (57) ABSTRACT

The invention is directed to an apparatus and a process for electropolishing a product or metallic device made from a metal alloy. The electropolishing apparatus includes a cathode formed of a tubular member and an anode formed by the metallic device to be electropolished. Both the tubular member and the metallic device are positioned within an electrolytic solution and current is passed through the anode to effect the electropolishing process. The invention is useful for electropolishing metal stents formed of metallic alloys, such as cobalt-chromium-tungsten, in which the stent is positioned within the tubular member and immersed in an electrolytic solution for a predetermined time. The electropolishing process using the apparatus of the invention provides an ultrasmooth and shiny metallic surface on the metallic device for metal stents.

14 Claims, 4 Drawing Sheets

APPARATUS FOR ELECTROPOLISHING A STENT

BACKGROUND OF THE INVENTION

The invention relates generally to providing an apparatus for electropolishing products made from metals. More particularly, the invention relates to an apparatus for electropolishing medical devices made of titanium, stainless steel, tungsten, nickel-titanium, tantalum, cobalt-chromium-tungsten, or cobalt-chromium.

While a wide range of products or devices can be made from the listed metal alloys for use with the present invention, medical devices are particularly suitable due to the biocompatible characteristics of these alloys. Thus, for example, implantable medical devices or devices that are used within the human body are particularly suitable and can be made from these alloys that have been electropolished in accordance with the present invention. More particularly, and as described in more detail herein, intravascular stents can be made from the listed alloys that have been electropolished according to the invention. Thus, while the description of prior art devices and of the invention herein refers mainly to intravascular stents, the invention is not so limited to medical products or intravascular stents.

Stents are generally metallic tube shaped intravascular devices which are placed within a blood vessel to structurally hold open the vessel. The device can be used to maintain the patency of a blood vessel immediately after intravascular treatments and can be used to reduce the likelihood of development of restenosis. Expandable stents are frequently used as they may travel in compressed form to the stenotic site generally either crimped onto an inflation balloon or compressed into a containment sheath in a known manner.

Metal stents can be formed in a variety of expandable configurations such as helically wound wire stents, wire mesh stents, weaved wire stents, metallic serpentine stents, or in the form of a chain of corrugated rings. Expandable stents, such as wire mesh, serpentine, and corrugated ring designs, for example, do not possess uniformly solid tubular walls. Although generally cylindrical in overall shape, the walls of such stents are perforated often in a framework design of wire-like elements or struts connected together or in a weave design of cross threaded wire.

Expandable stents formed from metal offer a number of advantages and are widely used. Metallic serpentine stents, for example, not only provide strength and rigidity once implanted they also are designed sufficiently compressible and flexible for traveling through the tortuous pathways of the vessel route prior to arrival at the stenotic site. Additionally, metallic stents may be radiopaque, thus easily visible by radiation illumination techniques such as x-ray film.

It is highly desirable for the surface of the stent to be extremely smooth so that it can be inserted easily and experience low-friction travel through the tortuous vessel pathway prior to implantation. A roughened outer surface may result in increased frictional obstruction during insertion and excess drag during travel to the stenotic site as well as damaging the endothelium lining of the vessel wall. A rough surface may cause frictional resistance to such an extent as to prevent travel to desired distal locations. A rough finish may also cause damage to the underlying inflation balloon. A less rough finish decreases thrombogenicity and increases corrosion resistance.

Stents have been formed from various metals including stainless steel, tantalum, titanium, tungsten, nickel-titanium which is commonly called Nitinol, and alloys formed with cobalt and chromium. Stainless steel has been extensively used to form stents and has often been the material of choice for stent construction. Stainless steel is corrosion resistant, strong, yet may be cut into very thin-walled stent patterns.

Cobalt-chromium alloy is a metal that has proven advantages when used in stent applications. Stents made from a cobalt-chromium alloy may be thinner and lighter in weight than stents made from other metallic materials, including stainless steel. Cobalt-chromium alloy is also a denser metal than stainless steel. Additionally, cobalt-chromium stents are nontranslucent to certain electromagnetic radiation waves, such as x-rays, and, relative to stainless steel stents, provide a higher degree of radiopacity, thus being easier to identify in the body under fluoroscopy.

Metal stents, however, suffer from a number of disadvantages. They often require processing to eliminate undesirable burrs, nicks, or sharp ends. Expandable metal stents are frequently formed by use of a laser to cut a framework design from a tube of metal. The tubular stent wall is formed into a lattice arrangement consisting of metal struts with gaps there between. Laser cutting, however, typically is at high temperature and often leaves debris and slag material attached to the stent. Such material, if left on a stent, would render the stent unacceptable for implantation. Treatment to remove the slag, burrs, and nicks is therefore required to provide a device suitable for use in a body lumen.

Descaling is a first treatment of the surface in preparation for further surface treatment such as electropolishing. Descaling may include, for example, scraping the stent with a diamond file, followed by dipping the stent in a hydrochloric acid or an HCl mixture, and thereafter cleaning the stent ultrasonically. A successfully descaled metal stent should be substantially slag-free in preparation for subsequent electropolishing.

Further finishing is often accomplished by the well known technique of electropolishing. Grinding, vibration, and tumbling techniques are often not suited to be employed on small detailed parts such as stents.

Electropolishing is an electrochemical process by which surface metal is dissolved. Sometimes referred to as "reverse plating," the electropolishing process actually removes metal from the surface desired to be smoothed. The metal stent is connected to a power supply (the anode) and is immersed in a liquid electrolytic solution along with a metal cathode connected to the negative terminal of the power supply. Current is applied and flows from the stent, causing it to become polarized. The applied current controls the rate at which the metal ions of the anodic stent are generally removed and diffused through the solution to the cathode.

The rate of the electrochemical reaction is proportional to the current density. The positioning and thickness of the cathode in relation to the stent is important to make available an even distribution of current to the desired portion of the stent sought to be smoothed. For example, some prior art devices have a cathode in the form of a flat plate or a triangular or single wire loop configuration, which may not yield a stent or other medical device with a smooth surface on all exposed surfaces. For example, the prior art devices do not always provide a stent having a smooth surface on the inner tubular wall of the stent where blood flow will pass.

The straightforward application of current, however, does not necessarily translate to even distribution of current across the entire surface sought to be polished. One important feature to creating an even surface on the desired portion of the part is the formation of current differential during the electropolishing process across the surface. Electropolishing provides varied current density to the surface imperfections such as undulations creating protrusions and valleys on the surface. Current density is highest at high points on the surface and lowest at the low points. The increased current density at the raised points causes the metal to dissolve faster at these points thus leveling the surface while forming a corrosion-inhibiting oxide layer.

Electropolishing in the proper electrolytic solution, can serve to smooth out the exposed rough surface to the point where it is ultrasmooth, shiny, and reflective. However, heretofore there has been no effective method to consistently produce an ultrasmooth, shiny finish on the surface a stent comprised of any metal or metal alloy such as cobalt-chromium alloys.

Treated with traditional electrolytic or etching solutions, such as those specified in ASTM E407-93, ASTM340-95, and ASTM E1558-93, a stent formed of metal alloy may exhibit a variety of finishes that may include a rather rough and unfinished appearance, a matte finish which is pitted, brown, blackened, feathered, etched, dimpled, rough, and/or uneven.

What is needed is an apparatus and a process for treating a product or device made of a metal alloy to consistently produce an ultrasmooth surface. The present invention satisfies this need.

SUMMARY OF THE INVENTION

The invention is directed to an apparatus and a process of electropolishing a product or device made from a metal alloy. More particularly, the product or device is suitably made from an alloy of stainless steel, titanium, nickeltitanium (Nitinol), tungsten, tantalum, cobalt-chromium-tungsten, or cobalt-chromium and is particularly useful for medical devices such as medical implants, hipjoints, bone screws, guide wires, catheters, filters, and intravascular stents. Other products and devices unrelated to the medical device products described herein also will benefit from the electropolishing apparatus and process when such products or devices are made from the listed metal alloys. Since the electropolishing apparatus and process of the invention are particularly useful for medical devices, and more particularly useful for intravascular stents, the process is described herein with respect to stents, but is not so limited.

The invention is directed to an improved product or device, such as a stent, formed from a metal alloy, that possesses an ultrasmooth shiny exterior surface. This invention is also directed to an apparatus for electropolishing such a stent using an acidic electrolytic solution to produce an exceptionally smooth surface. This invention also contemplates use of a composition of the electrolytic solution that serves to produce the ultrasmooth surface.

In keeping with the invention, an apparatus is provided, along with a process, for electropolishing a device made from a metal alloy. More particularly, the electropolishing apparatus includes a cathode and an anode submerged in an electrolytic solution for the purpose of removing metal from the surface of the metal alloy. The cathode design is intended to substantially surround the anode, which is the device made from the metal alloy, to remove metal from all exposed surfaces.

In one embodiment, a wire coiled in a spiral or helix configuration is submerged in a container of an electrolytic solution. The device, for example, an intravascular stent is the anode and is positioned within the coil and a current is applied from the anode, polarizing it, and thus encouraging metal ions of the stent to diffuse through the solution to the cathode. As the metal ions from the stent continue to diffuse, the surface irregularities diminish such that, after a predetermined time period, the surface of the stent becomes ultrasmooth and shiny. Importantly, all of the exposed surface area of the stent, including the outer and inner surfaces of the stent are polished smoother than a stent polished using conventional methods of electro-polishing. It is important for the outer tubular surface and the inner tubular surface of the stent to be smooth, since the outer surface contacts the vessel or arterial wall, and the inner surface is in contact with the blood flowing through the vessel or artery.

In another embodiment, a cylindrical tube formed of a mesh or weave configuration is provided as the cathode which is subsequently submerged or immersed in an electrolytic solution. As previously described, the stent, which is the anode, is then positioned within the cylindrical wire mesh tube for purposes of electropolishing the stent. A current is applied and flows from the anode (stent), polarizing it, and thus encouraging the metal ions of the stent to diffuse through the solution to the wire mesh tube cathode. After a predetermined time, the entire outer surface of the stent becomes ultrasmooth and shiny.

Other features and advantages of the invention will become apparent from the following detailed description, taken in conjunction with the accompanying drawings, which illustrate, by way of example, the features of the invention.

DETAILED DESCRIPTION OF THE PREFERRED EMBODIMENTS

The present invention is directed to an apparatus for electropolishing a metallic device utilizing a novel cathode design. More specifically, the new and improved cathode is used to substantially or completely surround a metallic device, which is the anode, and provide a more uniformly electropolished surface. By substantially surrounding the metallic device being electropolished, substantially all exposed surfaces of the device are electropolished. Further, the cathode does not need to completely surround the stent, neither radially or longitudinally.

In one embodiment of the invention, a tubular member is provided to surround the metallic device to be electropolished. By referring to a tubular member, it is not meant to be limiting and configurations other than a tubular member may be more suitable depending on the shapes of the metallic device being electropolished. Thus, the cathode can take other shapes and configurations depending upon the design of the metallic device being electropolished.

Figure 1:
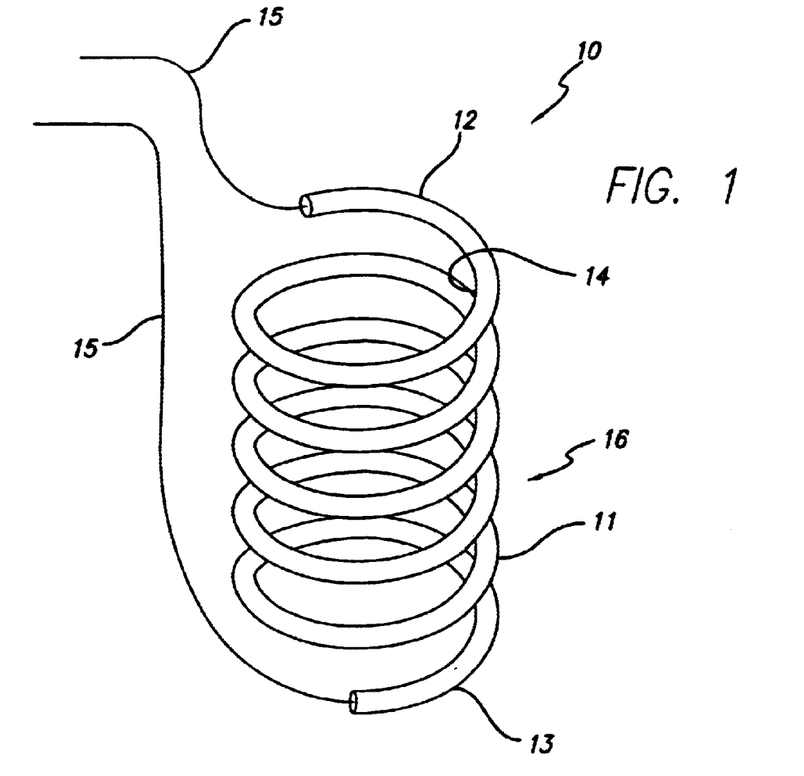
FIG. 1 is a schematic diagram of a coil wire forming the cathode of the electropolishing apparatus of the invention.
Figure 2:
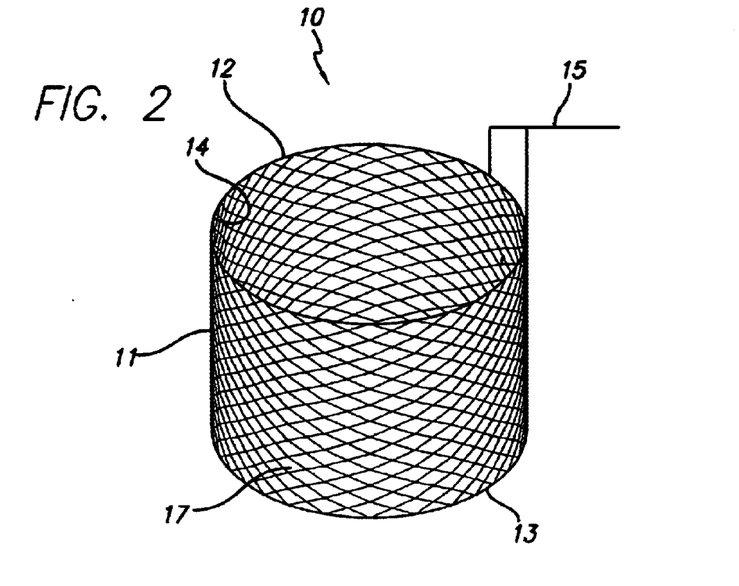
FIG. 2 is a schematic diagram depicting a wire mesh tubular member which is the cathode of the electropolishing apparatus of the invention.

In keeping with the invention, and referring to FIGS. 1 and 2, a cathode 10 is provided in the form of a tubular member 11. The tubular member has a first end 12 and a second end 13, with an opening 14 extending therethrough from the first end to the second end. In one embodiment as depicted in FIG. 1, a wire 15 is attached to a wire coil 16 that is generally in the shape of a helix or a spiral. In another embodiment, as shown in FIG. 2, the tubular member is in the form of a wire mesh tube 17 in which a lattice-type mesh extends substantially from the first end to the second end of the tubular member. While the tubular member 11 of FIG. 2 is in the form of a continuous wire mesh tube 17, the tube can be non-continuous (e.g., two or more arcuate sections with a longitudinal space between sections) and still operate as the cathode. Further, tube 17 can have other configurations such as an hour glass shape or a tapered shape to suit a particular application.

Figure 3:
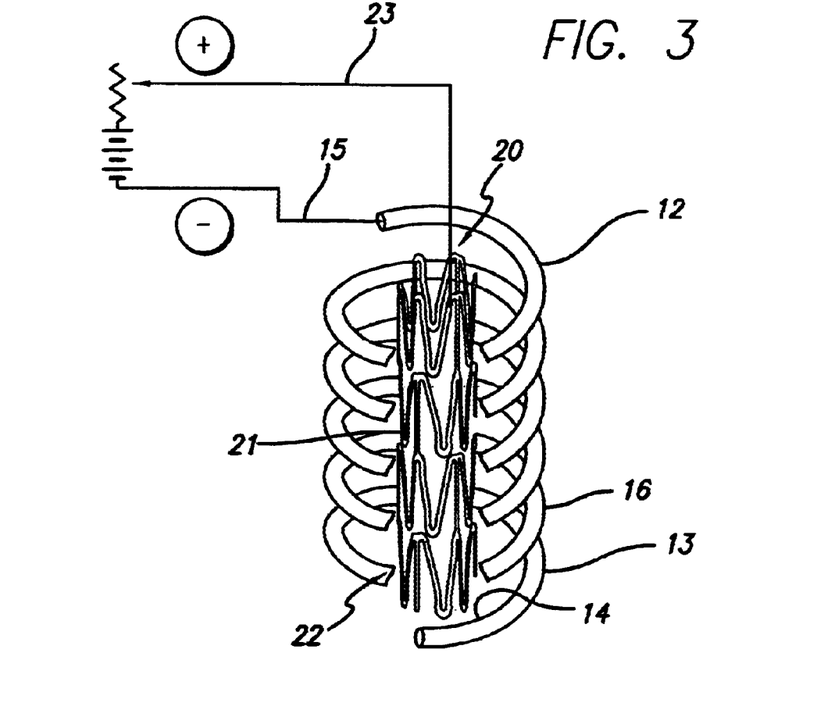
FIG. 3 is a schematic diagram depicting the wire coil with a metallic device anode position within the wire coil.
Figure 4:
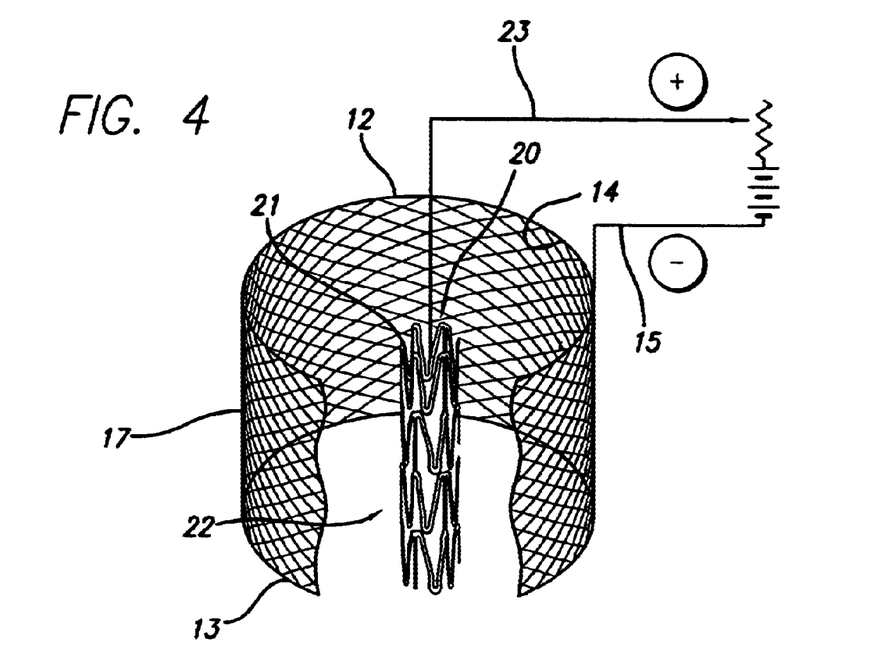
FIG. 4 is a schematic diagram depicting the wire mesh tubular member cathode with a metallic device anode positioned within the tubular member.

In further keeping with the invention, as shown in FIGS. 3 and 4, an anode 20 is formed by a metallic device 21. For purposes of discussion, and by illustration only, a metallic stent 22 is depicted as forming the metallic device. A current conducting member 23 (such as a wire) is attached to one end of the metallic device in order to complete the electrical circuit between the anode and cathode. Importantly, and as shown in the drawings, the cathode or tubular member substantially surrounds the anode or metal device. For example, the metallic device has a length and a diameter such that the length and diameter of the tubular member is greater than the length and diameter of the metallic device. As a more specific example, a typical coronary stent 22 can range in length from approximately 6 mm to 40 mm and have an unexpanded diameter in the range of about 1.5 mm to 7 mm, depending upon the application. In order to substantially surround the metal stent, the tubular member should have a length in the range of about 10 to 60 mm and a diameter in the range of about 4 to 70 mm. Obviously, these dimensions for the metallic device and the tubular member can vary widely depending upon the application and the size of the metallic device being electropolished. Further, the invention is not limited to electropolishing medical devices, rather it is useful for any type of metallic device capable of being electropolished and requiring an ultrasmooth surface.

Figure 5A:
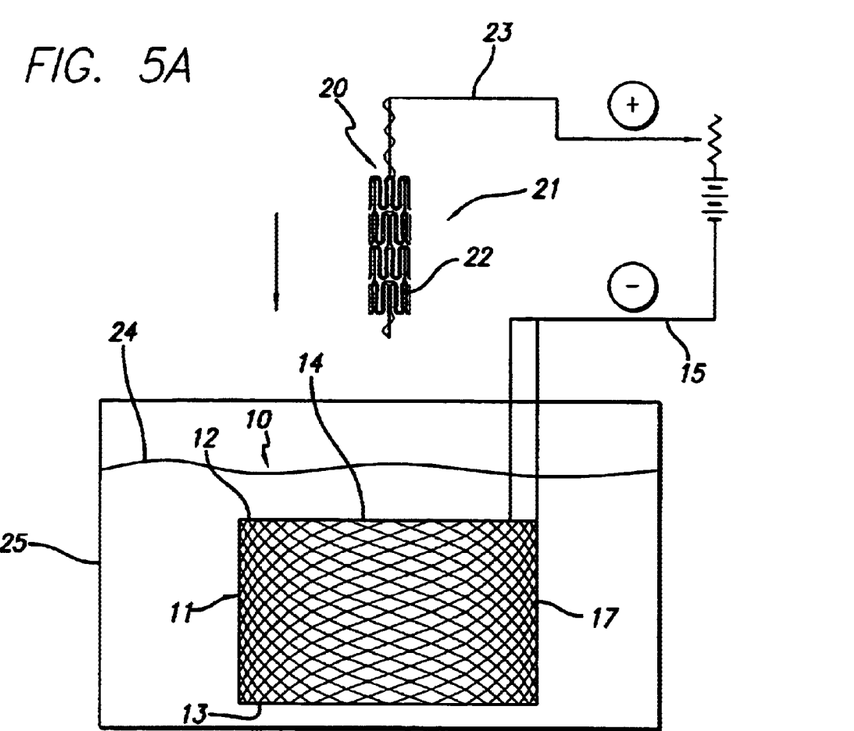
FIGS. 5A and 5B are schematic diagrams of the electropolishing apparatus of the present invention.
Figure 5B:
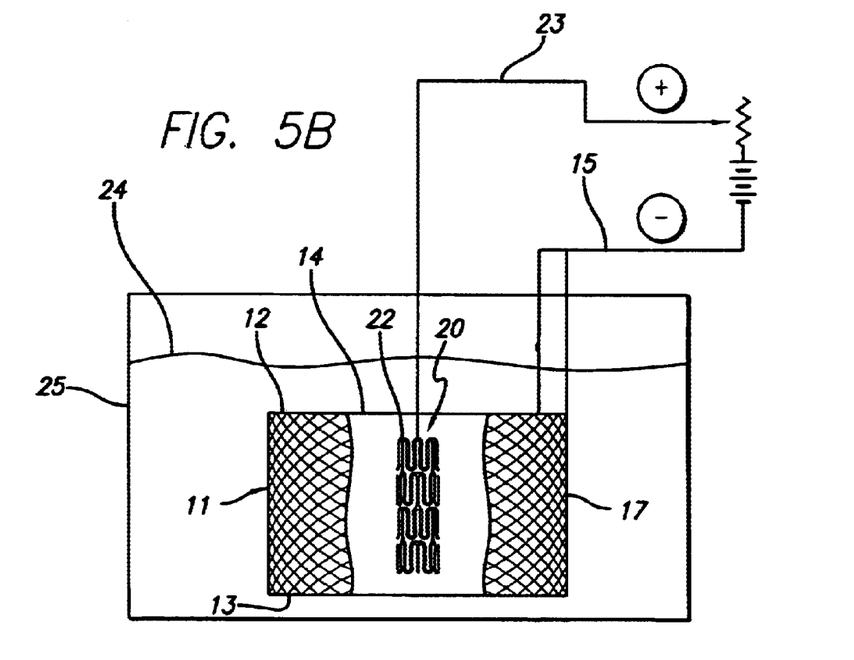

In order to accomplish the electropolishing process, the cathode 10 and anode 20 are submerged in an electrolytic solution. Turning to FIG. 5A, the cathode or tubular member 11 is shown submerged in an electrolytic solution 24 which is held in a container 25 that is commonly known. The anode 20 or metallic device 21 has not yet been submerged in the electrolytic solution and positioned within the tubular member. Turning to FIG. 5B, the electropolishing process is commenced when the anode or metallic device is positioned within the tubular member, in this case wire mesh tube 17, by positioning the metallic device substantially within the wire mesh tube. The composition of the electrolytic solution, and the amount of time that the metallic device is exposed to the electropolishing process, is a matter of choice depending upon the particular application. In order to illustrate the electropolishing process in more detail, the following describes electropolishing a cobalt-chromium stent 22 in a specific electrolytic solution. The following examples are for illustration purposes only, and are not intending to be limiting as to the type of metallic device that is to electropolished, nor limiting as to the electrolytic solution and the times and temperatures used to complete the process.

The cobalt-chromium stent 22 is formed from an alloy composed of cobalt and chromium comprising at least fifty percent by weight of the alloy and including one or more of a variety of metals and elements as is known in the art including, but not limited to nickel, titanium, tantalum, iron, nickel-titanium, tungsten, manganese, molybdenum, silicon, carbon, phosphorous, sulfur and nitrogen. In one embodiment, an alloy of Co—Cr—W (cobalt-chromium-tungsten) was evaluated. Cobalt-chromium stents can be made from alloys known in the art by the trade names Haynes®25, L605, and Stellite 25. Alternatively, the improved stent may be formed with an exterior metal surface comprised of an alloy of cobalt and chromium.

Typically, a cobalt-chromium stent incorporates a desired lattice configuration usually laser cut from a tube of cobalt-chromium alloy. During the laser cutting process, frequently much of the tube is cut away, to produce a chain of ring-like elements comprised of struts in a wave-like pattern with gaps therebetween and links connecting the ring elements together to form an elongated tubular body typically between 6 mm and 40 mm long. Implanted stents have an internal diameter typically between 2 mm for small vessel stents and up to 8 mm for larger vessels. Crimpable or expandable stents in a compressed condition typically have an internal diameter in the range of just under 1 mm to about 2 mm. Before surface treatment, the thickness of the stent wall is usually between 0.10 mm and 0.20 mm. All of these dimensions can vary to suit a particular application.

Such precision laser cutting, however, typically is at high temperature and often leaves debris and slag material attached to the stent requiring processing to eliminate it. Such debris and excess slag often exhibits itself in the form of undesirable bulges of material, burrs, nicks, and sharp ends. The stent is typically descaled by scraping it gently with a diamond file to avoid damaging the stent struts followed by dipping the stent in 37% concentrated hydrochloric acid (HCl or (HCl solutions) for approximately 5 minutes. Multiple stents may be so dipped into a test tube of HCl. In one embodiment, the stent is immersed in a solution of HCl:H2O2 at room temperature. The HCl solution can be repeatedly used until it turns dark green (from contaminants). Stents should be dipped slowly in fresh HCl as the HCl may react violently with them. In lieu of hydrochloric acid, other acids may be used to descale the stent including nitric acid (HNO3), phosphoric acid (H3PO4), or sulfuric acid (H2SO4), or other acidic solutions.

The descaling procedure is thereafter completed by rinsing and drying the stent. The stent is ultrasonically rinsed in water, preferably distilled water at about 58° Celsius, for about two minutes and then air dried. A procedure for preparing such a stent for implantation includes descaling and electropolishing the stent.

If examination under a microscope reveals residual slag the descaling process of scraping, acid bathing, ultrasonic rinsing, and drying should be repeated. Typically, a batch of five stents can be descaled in three to five cycles. A successful descaling of the stent should yield slag-free stents in preparation for subsequent electropolishing. Should small spots of slag stubbornly cling to the stent, they can be electropolished away without any adverse effects and without employing further descaling cycles to remove them.

Descaling yields a roughened, but clean surface available for further finishing by the well known technique of electropolishing. Stents being relatively small and fragile are well suited to electropolishing, but not to grinding, vibration, or tumbling to attain a smooth finish.

Sometimes referred to as "reverse plating," the process of electropolishing actually removes metal from the surface desired to be smoothed. Electropolishing is an electrochemical process to smooth metal surfaces by dissolution of metal, which takes place more rapidly at high points on the metal surface. The metal stent 22 is rendered anodic (+) 20 and is immersed in a liquid electrolytic solution 24 along with a metal cathode (−) 10. Current is applied and flows from the anode, polarizing it, thus encouraging the metal ions of the stent to diffuse through the solution to the cathode.

A special feature of electropolishing is the creation of current differentials across the microscopic surface of the anode. The current density is greatest at high points on the surface and lowest at the low points. The rate of the electrochemical reaction is directly proportional to the current density so that increased current density at the raised points causes the anodic metal to dissolve faster at these points thus leveling the surface material. The smoothed surface of many metals can, with sufficient electropolishing techniques including use of the proper electrolytic solution, be made sufficiently smooth to an extent as to become shiny and reflective. The finish may also be dependant on the level of current applied, the duration of applied current, and the temperature of the electrolytic solution.

In preparation for the electropolishing of the stent 22, the electrolytic solution 24 is prepared. While under a vented hood, and at standard conditions, 10 ml of 37% concentrated hydrochloric acid (HCl) is poured into a 50 ml beaker or container. 30 ml of 98% concentrated sulfuric acid ($H_2SO_4$) is then poured gradually into the HCl at a rate of about 1.5 ml per second to prevent a violent reaction. Both acids, whether individually or as a mixture, are extremely corrosive. Contact with skin or tissue, whether through liquid spill or in the form of exposure to fumes, can be severely injurious. Appropriate safety gear should be employed when handling and disposing of such acids.

Forming the anode 20, the stent 22 in one embodiment is 18 mm long and is mounted on a stainless steel, titanium or other metallic mandrel, which is conductively attached to a stainless steel clip. As is known in the art, there are a wide range of stent lengths available and reference to an 18 mm long stent is for illustration only. The clip is conductively attached to a titanium rod to which the wire 23 is attached at the opposing end of the rod to the positive terminal of a controllable power supply capable of supplying two to seven amperes up to at twenty four volts DC. The amperage and voltage can vary and in one embodiment the power supply provides three to seven amperes at up to twenty one volts.

Wire 15 is attached to the negative terminal of the power supply and is terminated at the cathode 10, such cathode formed from 90% Platinum and 10% Iridium clad over a Niobium core. For use with an 18 mm long stent, for example, the cathode or tubular member 11 is about 20 to 50 mm long and 4 to 70 mm in diameter and is submerged into the acid mixture so that the tubular member is suspended substantially in the acid. The anodic stent 22 is then lowered and vertically submerged into the electrolytic acid mixture 24 and positioned through the tubular member so that the ends of the stent are substantially equidistant from the tubular member. The clip remains out of the solution. The power supply is thereafter energized and adjusted altering the current controller to supply four amperes of current to the solution for a period of approximately ten seconds. While the disclosed embodiment shows stent 22 submerged in a vertical orientation, it can be rotated into other orientations such as, for example, from 0° to 90° relative to vertical.

The stent 22 is then removed from the electrolytic solution 24, rinsed with water, and turned axially on the mandrel to expose the stent surface beneath the mandrel contacts to the acid. The remounted stent is then resubmerged in the acid for additional cycles of electropolishing with another rinse and another turn relative to the mandrel. Longer stents have more surface area than shorter stents and may require more time in the acid solution and optimal results for any particular size and length of stent can easily be determined. The length of time the product or stent is in the solution is proportional to the surface area being electropolished. The greater the surface area, the more time the product or stent is exposed to the solution. The stent is thereafter cleaned ultrasonically in a distilled water bath at a temperature of 58° Celsius and subsequently air dried.

In one example using the invention, a number of cobalt-chromium stents 22 about 18 mm long and about 1.8 mm in outer diameter were electropolished by submerging the stents in an electrolytic solution and within the tubular member 11 (cathode). The tubular member in this embodiment was about 36 to 40 mm high (or long) and about 14–20 mm in diameter. The stents were submerged for 8 second cycles at between 2 to 7 amps. The cycles were repeated for between 8 to 20 times to provide ultrasmooth stents.

The ratio of the height of the cathode to stent length can range from about 1:1 to about 8:1. At a 1:1 ratio, the stent ends are likely to be polished less than at a ratio of 8:1. The ratio of the tubular member diameter to the stent diameter can range from about 5:1 to about 10:1. Cycle times also can vary and range from 6 to 8 seconds for cobalt-chromium stents that are about 18 mm in length.

The present invention electropolishing apparatus also optionally includes means for circulating the electropolishing solution through the stent 22 and the tubular member 11. Various devices can be used to circulate the electrolytic solution and can include, for example, a circulation pump for rotating or oscillating, a stir bar, or a re-circulation pump. It is preferred that the solution be gently moved as opposed to a vigorous movement so that it does not interfere with the electropolishing process.

The electropolishing procedure employing the solution of the present invention removes material from the stent surface to provide an ultrasmooth and shiny surface. Electropolishing also provides a protective corrosion-resistant oxide layer on the stent surface.

Figure 6:
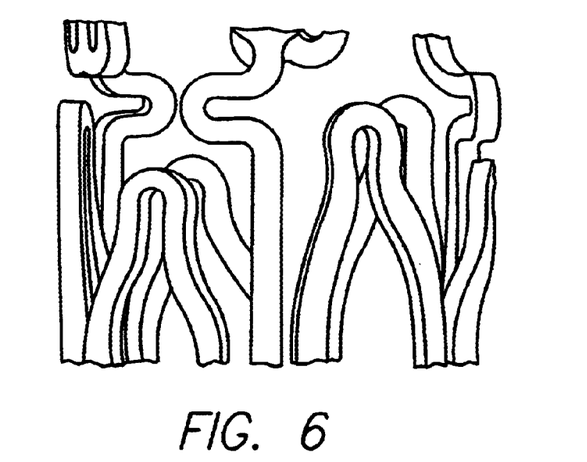
FIGS. 6–8 are photomicrographs depicting the surface of a portion of a stent electropolished with the apparatus of the present invention.
Figure 7:
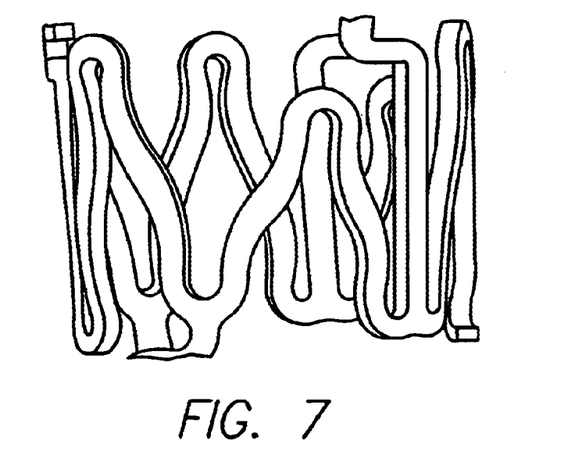
Figure 8:
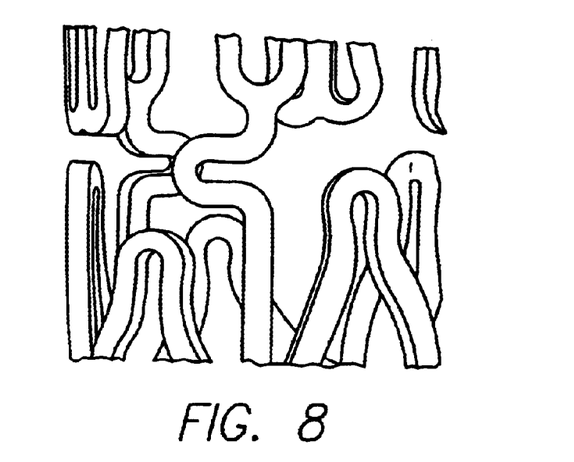

FIGS. 6–8 illustrate, in the form of enlarged photomicrographs taken with a scanning electron microscope (SEM), strut surfaces of a cobalt-chromium stent 22 of the present invention electropolished using the apparatus of the present invention. FIGS. 6–8 reveal ultrasmooth and shiny strut surfaces.

As is the nature of many parameters of various processes, parameters of the electropolishing process may be altered by degree to provide similar results. It is the intention to include such modification, within the scope of the invention, and as is known in the art, of time, temperature, humidity, pressure, voltage, current, cathode material, cathode dimension, degree of descaling, rinsing, polishing/solution chemicals, size and material composition of the medical device or stent, as well as other variable parameters not heretofore mentioned.

The embodiments heretofore discussed are in no way intended to limit the scope of the invention. Various changes and improvements may also be made to the invention without departing from the scope thereof.

What is claimed:

1. An apparatus for electropolishing a stent, comprising:
   a continuous cathode formed by a tubular member having a first end and a second end defining a length, a diameter, and an opening therethrough;

a current conducting member attached to the tubular member first end and second end;

an anode formed by a metallic stent having a first end and a second end defining a length, and a diameter, the stent being positioned within the tubular member opening;

the ratio of the length of the tubular member to the length of the stent ranges from about 1:1 to about 8:1 and the ratio the tubular member diameter to the stent diameter ranges from about 5:1 to about 10:1;

an electrolytic solution; and the tubular member and the stent being substantially submerged in the electrolytic solution and a current source attached to the stent to conduct a current through the stent for a predetermined time to electropolish the stent.

2. The apparatus of claim 1, wherein the tubular member is formed from a metal wire shaped in a helical coil configuration.

3. The apparatus of claim 1, wherein the tubular member is formed from a wire mesh.

4. The apparatus of claim 1, wherein the tubular member is formed from at least one metal wire shaped in a ring configuration.

5. The apparatus of claim 1, wherein the tubular member is cylindrical.

6. The apparatus of claim 1, wherein the tubular member is non-circular.

7. The apparatus of claim 1, wherein the tubular member has an hourglass configuration.

8. The apparatus of claim 1, wherein the stent is made from a metal alloy taken from the group of metal alloys including stainless steel, cobalt-chromium, cobalt-chromium-tungsten, nickel-titanium, titanium, tantalum, and tungsten.

9. The apparatus of claim 1, wherein means for circulating the electrolytic solution is provided.

10. The apparatus of claim 9, wherein a pump circulates the electrolytic solution.

11. The apparatus of claim 9, wherein the electrolytic solution is circulated mechanically.

12. An apparatus for electropolishing a stent, comprising:

a continuous cathode formed by a tubular member having a first end and a second end defining a length, a diameter, and an opening therethrough, the tubular member having a wall surface between the first end and the second end and a plurality of apertures formed in the wall surface;

a current conducting member attached to the tubular member first end and second end;

an anode formed by a metallic stent having a first end and a second end defining a length, and a diameter, the stent being positioned within the tubular member opening;

the ratio of the length of the tubular member to the length of the stent ranges from about 1:1 to about 8:1 and the ratio the tubular member diameter to the stent diameter ranges from about 5:1 to about 10:1;

an electrolytic solution for flowing through the tubular member apertures; and the tubular member and the stent being substantially submerged in the electrolytic solution and a current source attached to the stent to conduct a current through the stent for a predetermined time to electropolish the stent.

13. The apparatus of claim 12, wherein means for circulating the electrolytic solution is provided.

14. An apparatus for electropolishing a stent, comprising:

a continuous cathode formed by a wire mesh tubular member having a first end and a second end defining a length, a diameter, and an opening therethrough;

a current conducting member attached to the tubular member first end and second end;

an anode formed by a metallic stent having a length and a diameter, the stent being positioned within the tubular member opening;

the ratio of the length of the tubular member to the length of the stent ranges from about 1:1 to about 8:1 and the ratio the tubular member diameter to the stent diameter ranges from about 5:1 to about 10:1;

an electrolytic solution; and the tubular member and the stent being substantially submerged in the electrolytic solution and a current source attached to the stent to conduct a current through the anode for a predetermined time to electropolish the stent.

\* \* \* \* \*

UNITED STATES PATENT AND TRADEMARK OFFICE
CERTIFICATE OF CORRECTION

PATENT NO. : 6,679,980 B1
DATED : January 20, 2004
INVENTOR(S) : Anthony Andreacchi It is certified that error appears in the above-identified patent and that said Letters Patent is hereby corrected as shown below:

Column 4,
Line 8, delete "electro-polishing" and insert -- electropolishing --.

Column 5,
Line 62, delete "intending" and insert -- intended --.
Line 63, after "that is to" insert -- be --.

Column 6,
Line 35, delete the open parenthesis before "HC1 solutions".

Column 7,
Line 44, delete "up to at" and insert -- at up to --.

Column 9,
Line 4, after "length" delete the comma.

Column 10,
Line 7, after "length" delete the comma.

Signed and Sealed this

Sixth Day of July, 2004

JON W. DUDAS
*Acting Director of the United States Patent and Trademark Office*